United States Patent [19]

Steinman

[11] Patent Number: 5,641,746

[45] Date of Patent: Jun. 24, 1997

[54] ANIMAL MODEL FOR AIDS

[75] Inventor: Judith L. Steinman, Jersey City, N.J.

[73] Assignee: Rutgers State University of New Jersey, New Brunswick, N.J.

[21] Appl. No.: 254,041

[22] Filed: Jun. 3, 1994

[51] Int. Cl.$^6$ .............. A61K 38/08; C07K 7/06

[52] U.S. Cl. .............. 514/12; 514/16; 530/328; 530/868

[58] Field of Search ............ 514/12, 16; 530/328, 530/868

[56] References Cited

PUBLICATIONS

Yaksh, T.L., et al., *Science* 192 (1976) 1357–1358.
Hill, J.M., et al., *Brain Res.*, 603(2) (1993) 222–233.
Brenneman et al. *Nature* 335 (1988) 639–642.
Brenneman et al., *Drug Dev. Res.* 15 (1988) 361–369.
Muller et al., *Eur. J. Pharm.* 226 (1992) 209–214.
Glowa et al., *Brain Res* 570 (1992) 49–53.
Pert et al., *PNAS*, 83 (1986) 9254–9258.
Bridge, T.P., et al., *Lancet II* (1989) 226–227.
Steinman, et al., (abstr.) IXth International Conference on AIDS, Berlin (1993).
Dreyer, E.B., et al., *Science*, vol. 248, (1990) 364–367.
Gibbons, A., *Science*, "Is AIDS Dementia Due to Increases in Calcium?" (Apr. 20, 1990) 303.
Dawson, V.L. et al., (abstr.) *Society for Neuroscience*, vol. 18 (1992) 321.1.

*Primary Examiner*—Paula K. Hutzell
*Assistant Examiner*—Benet Prickril
*Attorney, Agent, or Firm*—Cobrin Gittes & Samuel

[57] ABSTRACT

A method of inducing symptoms similar to those in AIDS-infected individuals, particularly neurological deficit, wherein peptide T, VIP or gp120 or a derivative or peptide analog thereof is intrathecally administered to non-human mammals.

28 Claims, No Drawings

ANIMAL MODEL FOR AIDS

BACKGROUND OF THE INVENTION

The present invention relates to inducing symptoms in non-human mammals similar to those in AIDS-infected individuals, particularly symptoms of neurological deficit, thereby creating an effective animal model for AIDS.

The development of effective anti-AIDS therapies depends to a large extent on the development and utilization of animal models for AIDS. The use of monkeys as a model for AIDS studies are of limited use. Given the prohibitive cost, only a limited number of monkeys are used per study. Furthermore, testing macaques infected with SIV, the causative agent of simian AIDS, may not be satisfactory because the same neurological deficits observed in human AIDS patients, e.g., dementia, are not observed. A transgenic mouse strain is currently available. The use of transgenic animals, however, is cost prohibitive.

Developing model in vivo systems generally involves the administration of the etiologic agent of AIDS, the HIV virus. Researchers and laboratory personnel may be wary of handling the infectious live virus to the detriment of furthering research in this area.

As such, potential anti-AIDS drugs are often sent directly to clinical trials without having been tested for side effects or efficacy in an animal model. Many more drugs than necessary are therefore likely to enter clinical trials without specifically targeting agents shown to be promising in animal models. Human clinical studies themselves are problematic in that in many instances they require patients to be free of the effects of the drug zidovudine (AZT), which can temporarily improve neurological symptoms seen with AIDS.

A model is thus needed which alleviates the above problems where data is generated in a timely fashion in order to permit potential anti-AIDS drugs to readily enter clinical trials.

Viruses may use endogenous peptide receptors to infect cells. The HIV virus has been shown to bind to a surface molecule known as the CD4 or T4 region, which is present on various cells susceptible to HIV infection, including T lymphocytes and macrophages.

Patients with AIDS exhibit not only symptoms arising from immunodeficiency, but also neuropsychological deficits. The central nervous and immune systems share a large number of specific cell-surface recognition molecules, serving as receptors for neuropeptide-mediated intercellular communication. The neuropeptides and their receptors show profound evolutionary stability, being highly conserved in largely unaltered form in unicellular as well as higher animals. Furthermore, the central nervous and immune systems show common CD4 (T4) cell-surface recognition molecules which serve as receptors for the binding of HIV envelope glycoprotein (gp 120). The gp120 glycoprotein has been shown to affix non-covalently to the brain membranes of humans, rats and monkeys and to cells of the immune system.

The envelope glycoprotein of the HIV virus, gp 120, has been associated with antigenicity, infectivity and neurotoxicity. HIV-induced neurotoxicity appears to be associated with gp 120-CD4 binding resulting in increased intracellular free calcium. Calcium channel blockers such as nimodipine have been shown to antagonize this effect. In vitro neurotoxicity of gp 120 has been described, for example, by Brenneman et al. *Nature* 335 (1988) 639–642; Brenneman et al. *Drug Dev. Res.* 15 (1988) 361–369; Dryer et al. *Science* 248 (1990) 364–367; and Dawson et al. *Soc. Neurosci* 18 (abstr)(1992) 321.1. Neurological deficits have been observed in neonatal rats following systemic administration of gp-120. Hill et al. *Brain Res.* 603(2) (1993) 222–223. Gp120 neurotoxicity of rat cortical neurons with apoptosis has also been described. Muller et al. *Eur. J. Pharm.* 226 (1992) 209–214. Direct injection of gp-120 to the cerebral ventricles was reported to result in memory impairments in adult rats. Glowa et al. *Brain Res.* 570 (1992) 49–53.

Peptide T is a modified octapeptide homologous to a subunit sequence of the endogenous Vasoactive Intestinal Peptide (VIP) described by Pert, et al. *Proc. Natl. Acad. Sci.* 83 (1986) 9254–9258 that was found to exist in homologous form in the 120 Kilodalton envelope glycoprotein (gp120) of all HIV isolates sequenced. Autoradiographic mapping with labelled gp120 has shown greater binding in VIP receptor rich areas. In vitro studies have demonstrated that VIP and peptide T inhibit both the binding of gp120 to brain tissue and HIV replication in cell culture. Intravenous peptide T in doses up to 224 mg/day has shown no toxicity and has resulted in improved neurocognitive functioning in the HIV-infected patients. Brenneman, D. et al. *Nature* 335 (1988) 639–642; Bridge, T P et al., *Lancet* 2 (1989) 226–227; Hill, J. M. et al. (abstr.) Sixth Intl. Conf. on AIDS vol. 1, page 330.

Peptide T has been reported to block gp120 binding to inhibit infectivity of patient primary viral isolates. VIP or peptide T potently inhibit the neurotoxic effects of gp120 on cells and in animals. While cortical neuronal loss and behavioral deficits have been reported in neonatal rats receiving gp120, Hill, J. M., et al. *Brain Res.* 603(2) (1993) 222–223, all of these abnormalities were reversed by co-administered peptide T.

The present invention provides a model for AIDS in non-human animals whereby symptoms similar to those in AIDS-infected individuals are induced, particularly symptoms of neurological deficit. Peptide T, VIP, gp120 or a derivative or peptide analog thereof is administered intrathecally to a non-human mammal in concentrations effective to induce these symptoms.

It is an object of the present invention to provide a model for AIDS in non-human mammals.

It is a further object of the present invention to provide a method of inducing symptoms similar to those in AIDS-infected individuals in non-human mammals, particularly rats.

It is an object of the present invention to provide a method of inducing neurological deficit in non-human mammals, particularly rats.

Moreover, it is an object of the present invention to induce the desired symptoms without the necessity of handling the live, infectious AIDS virus.

Finally, it is an object of the present invention to provide a reliable, cost-effective, relatively simple and time-efficient model for testing the effect of potential anti-AIDS drugs.

The above and other objectives, features and advantages of the present invention will become apparent to those skilled in the art from the following descriptions and are within the scope of the present invention.

SUMMARY OF THE INVENTION

The present invention provides a method of inducing symptoms in non-human mammals similar to those in AIDS-infected individuals in which peptide T, VIP or gp120 or a derivative or peptide analog thereof is administered intrathecally. In particular, the present invention provides a method of inducing neurological deficit in non-human mammals by this treatment. Peptide T, VIP or gp120 or a derivative or peptide analog thereof, is administered intrathecally in an amount effective to induce the desired symptoms. Administration with peptide T, VIP or a derivative or peptide analog of gp120 is preferred over gp120 as a more pronounced response is induced therewith.

Concentrations which are shown to be effective to induce the desired symptoms include 0.2 ng/ul gp120, 2.55 to about 5.0 ug/ul peptide T and 2.55–12 ug/ul VIP. Slow release of peptide T, VIP, gp120 or a derivative or peptide analog thereof may be effected by the present invention, thereby more accurately mimicking HIV infection. Potential anti-AIDS drugs may then be tested in the animal model as to their effect on the symptoms induced. Hence, anti-AIDS drugs with the utility desired, e.g., alleviation of neurological deficit, may be readily identified.

DETAILED DESCRIPTION OF THE INVENTION

The present invention recognizes that administration of gp120, the envelope protein of the HIV virus, induces symptoms in non-human mammals similar to those present in AIDS-infected individuals, e.g., specific neurological deficits, when administered directly to the spinal cord, i.e., intrathecally. Other compounds related to the envelope coat protein of HIV are also found to produce AIDS-like symptoms when administered intrathecally. Furthermore, specific neurological deficits are observed in animals treated with these compounds.

Administration of Gp120

Ten rats under anesthesia were prepared by inserting intrathecal (IT) catheters of commercially available PE10 polyethylene tubing, 7 cm., into the subarachnoid space of the spinal cord via incision in the cisterna magna membrane. One end of the tube was placed at the lower spinal cord region and the other end of the tube was left exposed through the skin in order to inject the desired agent directly into the subarachnoid space. The procedure is provided in further detail in Yaksh and Rudy *Science* 192 (1976) 1357–1358. Note, however, that the volume administered here is 5 ul, rather than 20 ul, as specified therein.

After the animals recovered from surgery in about 7–10 days, 1 ng. gp120 in 5 ul. saline (0.2 ng/ul) was infused through the tubes to the lower spinal cord region of each rat. Motor performance (hindlimb and forelimb use, walking patterns) was videotaped before and up to 12 hours after rats received either gp-120 or vehicle alone. The experimenter was blind to treatment. After the response of the animals was observed for one hour, the experimenter successfully discerned which animals received treatment with gp120.

Seven of the ten rats receiving IT gp-120 showed monoparesis of either the right or left forelimb; none of the saline control rats exhibited paresis (Chi2=6.39, df=1, p 0.02 comparing the two treatment groups). The onset of monoparesis was variable (mean +/−sem=22.2+/−7.4 min.), appearing as early as 4 min. post IT injection. The mean recovery time was 6 hours. In 3 of the 7 rats, the monoparesis appeared intermittently during the first two hours, then persisted for the next 3–4 hrs; in the other 4 rats, monoparesis was continuously present from its onset. In 5 of the 7 rats, forelimb monoparesis was accompanied by hindlimb rigidity during walking or when pressure was placed manually against the footpad. At autopsy, it was found that the monoparesis was ipsilateral to the side of the spinal cord where the tip of the IT catheter was positioned. This points to the specificity of the effect of gp-120 in acting locally, at or near the level of the motorneurons, to produce forelimb paresis.

The treated rats were observed as having immediate hemiparesis (weakness of forelimb), generally as early as 4 minutes after infusion. Intrathecal administration of gp120 induces a reliable response (hemiparesis) within 1–60 minutes after injection. Additional symptoms which appear several hours after gp120 injection include hindlimb rigidity, arching of the back and difficulty walking. The response lasted approximately 7 hours.

These findings demonstrate that an envelope protein of HIV induces neurological motor deficits when administered directly to the spinal cord, providing a unique model for studying gp 120-induced neuronal deficits.

Administration of Peptide T and VIP

Rats were treated by the surgical procedure above described. Initially, tests were performed to determine whether peptide T produces an analgesic effect. This was the primary goal of the testing of Group I and Group II animals discussed below. Data is provided in regard to the unexpected illness of Group I animals, from which one animal died and the remaining animals were sacrificed. In Group 2 animals, observations were taken at certain time periods after administration of peptide T. Illness in these animals was also observed which resulted in the death or sacrifice of all animals.

In Group I animals, three doses of peptide T (per 5 ul. saline) were administered: 6.43 ug (molar equivalent to 25 ug VIP), 12.86 ug and 25 ug. Each animal was tested with drug at the two lower doses or saline control in a counterbalanced fashion. A summary of treatments is set forth in Table I as follows; note that these animals received multiple treatments:

TABLE I

| Group I - Summary of Treatments | | |
| --- | --- | --- |
| Rat. No. | Day # | Treatment |
| 1 | 1 | 6.43 ug peptide T |
|   | 12 | Saline |
|   | 20 | 12.86 ug peptide T |
|   | 30 | Saline |
|   | 32 | Euthanized |
| 2 | 1 | 6.43 ug peptide T |
|   | 12 | Saline |
|   | 20 | Saline |
|   | 30 | 12.86 ug peptide T |
|   | 32 | Euthanized |
| 3 | 1 | Saline |
|   | 12 | 6.43 ug peptide T |
|   | 20 | 12.86 ug peptide T |
|   | 30 | Saline |
|   | 32 | Euthanized |
| 4 | 1 | 6.43 ug peptide T |
|   | 12 | Saline |
|   | 20 | 12.86 ug peptide T |
|   | 30 | Saline |
|   | 32 | Euthanized |
| 5 | 1 | Saline |
|   | 12 | 6.43 ug peptide T |
|   | 20 | Saline |
|   | 21 | Discovered Dead |

Within Group I, rats 1, 3, 4 and 5 had received injections of peptide T the previous week (not listed). One rat (No. 5)

died 9 days after the administration of 6.43 ug. peptide T while the other rats in this group were euthanized due to profound illness. Rats 1 and 4 were euthanized 14 days after the 12.86 ug dose of peptide T (the 12.86 ug dose being 20 days after the administration of the specified 6.43 ug dose). Rat 3 was euthanized 14 days after the 12.86 ug dose (the 12.86 ug dose being 8 days after the specified 6.43 ug. dose). Rat 2 was euthanized two days after receiving the 12.86 ug dose (the 12.86 ug dose being 32 days after the 6.43 ug. dose). The cumulative administration of these treatments may have caused the illness which resulted in the death or sacrifice of Group I animals.

TABLE II

Group II - Summary of Treatment

| Rat. No. | Day # | Treatment | Observations |
| --- | --- | --- | --- |
| 6 | 1 | Saline | No response |
|  | 16 | 25 ug peptide T | N/A |
|  | 17 | — | Some blood and mucous around the eyes and nose; listless movements |
|  | 18 | — | Diarrhea; hemiparesis (left); blood around eyes and nose; dragging body to walk; extension of both hindlegs; difficulty righting; can grasp with left paw; general glassy appearance |
| 7 | 1 | Saline | No response |
|  | 16 | 25 ug peptide T | N/A |
|  | 17 | — | Some blood and mucous around the eyes and nose; listless movements |
|  | 18 | — | Diarrhea; failure to clean genital region; hemiparesis (right); general glassy appearance |
| 8 | 1 | 12.86 ug peptide T | N/A |
|  | 16 | — | Systemic illness; motor problems; perfused |
| 10 | 1 | 12.86 ug peptide T | N/A |
|  | 16 | — | Apparently healthy but jumpy |
| 12 | 1 | 12.86 ug peptide T | N/A |
|  | 7 | — | Discovered dead |

In the testing of Group II animals, either 12.86 or 25 ug peptide T was administered. The results are listed in Table II. Where no observations were taken, N/A is indicated. Of Group 2, three rats (Nos. 8, 10 and 12) received 12.86 ug. peptide T. Rat No. 12 was found dead 7 days later. Sixteen days after the 12.86 ug. treatment, rat No. 8 was ill and could not be tested. As noted, rat No. 10 was apparently healthy at sixteen days but jumpy.

Rat Nos. 6 and 7 were given saline as a control. No response was observed. Sixteen days later, while apparently healthy, these rats were given 25 ug. peptide T. Careful observations of these rats were made by two independent observers on the first and second day after treatment. One day after this treatment, both rats had some blood and mucous around the eyes and nose and were listless in their movements. These symptoms indicate that the animals were developing systemic illness, suffering from physiological stress and motor problems. The following day, their condition appeared to have worsened. Both rats lost approximately 10% of their body weight over 48 hours. Rat Nos. 6 and 7 were videotaped and sacrificed two days after administration of 25 ug peptide T. It was observed that the condition of rats 6 and 7, upon sacrifice, appeared similar to that of rat No. 8 upon sacrifice. Rat No. 8 had been given 12.86 ug. peptide T and was perfused 15 days after administration of this dose.

In each of these three rats (rat Nos. 6, 7 and 8), one forelimb was "favored" i.e., no weight was put on the limb and it was held in a constricted fist. However, the animals were able to grasp with the paw when put on a screen; the forelimbs appeared flaccid rather than paralyzed. Their backs were arched upward and each showed extension of their hindlegs. They dragged their tails and their hindlegs while walking, although they were able to walk. They had difficulty righting themselves when put on their backs and showed evidence of not cleaning their genital regions. Two of the rats had diarrhea. Rat Nos. 6, 7 and 8 were perfused intracardially with paraformaldehyde and intrathecal catheter position was documented. None were abnormal.

There did not appear to be significant elevations in pain thresholds in response to intrathecally administered peptide T at the doses and times mentioned for any of the Group I or II rats tested. Pain thresholds were assessed by tail flick latency to radiant heat, vocalization to electric shock of the tail and pinching of the skin with mouse-toothed forceps.

Note that observations of Group II rats during the initial demonstration of serious illness or neurological deficit were not made. Observations immediately after injection and at continuous time periods thereafter for up to 35 hours, 30 minutes were made for another rat. These observations are set forth in Table III.

TABLE III

Observation of a Rat Administered 25 ug Peptide T IT

| Post-Injection Time | Observation |
| --- | --- |
| 3 min. | Paraparesis (left); face is clean; able to use hindlegs, but keeping body low to ground; grooming (facial) with both paws; not vocalizing upon touch; able to walk on left paw, but when sitting, holds it in a fist and does not put pressure on it; able to right herself. |
| 1 hr. | No diarrhea; able to right herself. |
| 2 hrs. | Starting to arch back; keeping right forepaw under body for support; some diarrhea; starting to slow in righting, yet able to do so. |
| 3 hrs. | Diarrhea; vocalizing upon touch; paw not allodynic; hind feet splayed out at sides and under belly; holding head down; appears to feel ill. |
| 4 hrs. 45 min. | Back arched; does not vocalize to touch merely when picked up; foot not allodynic; slight withdrawal to pinch of left foot; pulls limbs equally to pinch; able to right herself. |
| 6 hrs. 45 min. | Blood around nose; arched back; diarrhea; able to right herself; hind feet under body. |
| 18 hrs. | Blood around nose; still hemiparetic; back arched up; breathing rapid and labored; squeaks to paw pinch; does not extend left rear leg as much as right when held in air. |
| 20 hrs. 20 min. | Turning towards left side; may be hyperventilating; problem (minor) with righting, but still able to do so; walks, always holding paw up. |
| 22 hrs. 20 min. | No diarrhea. |
| 26 hrs. | Diarrhea; can't right herself; hyperventilating (shallow, rapid breathing), hindpaws all the way up under her ribcage when she sits; righting problem is worse to left. |
| 29 hrs. | Breathing rapid and constant (appears to be shivering); keeps hind feet under torso to walk; both legs extend when she is held up; no longer vocalizing when picked up. |

TABLE III-continued

Observation of a Rat Administered 25 ug Peptide T IT

| Post-Injection Time | Observation |
| --- | --- |
| 30 hrs. | Blood around nose looks worse; breathing problem is constant; turning to left; withdraws and squeaks to pinch. |
| 32 hrs. | Waddling, still holding body close to floor; appears to be using her paw (left) a little more now. |
| 34 hrs. | Doesn't appear as sick as prior day; slight motor deficits with left hind paw; falling onto side, can't climb grid well; difficulty righting in both directions; moving around more than prior day. |
| 35 hrs. | Using left paw (front) to walk a little bit more. |
| 35 hrs. 30 min. | Can right herself, but not normally; rapid breathing; legs not extended when held up. |

Data from Table III indicates that upon treatment with 25 ug peptide T, hemiparesis was first observed at 3 minutes post-injection. At about 2 hours post-injection, righting problems and diarrhea were observed as hemiparesis continued. At about 6.5 hours, blood and mucous were first observed around the nose.

TABLE IV

Group IV - Summary of Treatment

| Rat No. | Time Symptoms Appeared Post-injection | Treatment | Observations |
| --- | --- | --- | --- |
| 1 | 12 minutes | 25 ug peptide T | Hemiparesis |
| 2 | 3 minutes | 25 ug peptide T | Hemiparesis |
| 3 | 22 minutes | 25 ug peptide T | Paresis of both forepaws |
| 4 | N/A | 5 ul d H$_2$O | No response |
| 5 | N/A | 5 ul d H$_2$O | No response |
| 6 | 24 minutes | 1 ng gp120 | Hemiparesis |
| 7 | N/A | 1 ng gp120 | No response |
| 8 | N/A | 20 ng gp120 | No response |
| 9 | N/A | 20 ng gp120 | No response |

A new treatment group was studied to further observe the latency of symptoms in rats after peptide T and gp120 administration. The treatments and observations are set forth in Table IV. Control animal Nos. 4 and 5 treated with vehicle alone demonstrated no sign of paresis throughout the 2 hour observation period. Rat Nos. 1, 2 and 3 were treated with 25 ug peptide T per 5 ul d H$_2$O (5 ug/ul). Hemiparesis or paresis of both forepaws occurred at 3 minutes, 12 minutes and 24 minutes post injection. These initial symptoms persisted from the time of onset continuously until at least 60 minutes post-injection during which time the animals were observed. Rat Nos. 6 and 7 were treated with 1 ng gp120 per 5 ul dH$_2$O (0.2 ng/ul). Rat No. 6 demonstrated hemiparesis at 24 minutes, whereas rat No. 7 showed no sign of paresis throughout a 2 hour observation period. Two rats were treated with gp120 at a much higher dose of 20 ng/5 ul (0.2 ng/ul). No response was observed, however.

It appears that peptide T at very low doses would not be effective. Rats treated with 1 ng gp120 exhibited paresis and were treated the next day with 1 ng gp120, again exhibiting these symptoms. Shortly thereafter, 0.1 ug peptide T in 5 ul saline was administered. These rats were not observed to be more ill than they were prior to this injection. Therefore, 0.1 ug peptide T in 5 ul (0.02 ug/ul) may be too low a dose to induce the symptoms desired.

In general, higher doses of peptide T induced a more robust effect than lower doses. The 12.86 ug peptide T dose produced a good response, yet the 25 ug peptide T dose produced a more immediate and reliable response. Accordingly, it is expected that even higher doses of peptide T would be effective. In the rat animal model, for instance, up to 50 ug peptide T per 5 ul (10 ug/ul) would likely produce a desirable response.

A response similar to that observed upon treatment with peptide T was also seen with VIP administered intrathecally. Each animal was treated with VIP or Ringer's solution in a counterbalanced fashion. No response was observed upon treatment with Ringer's solution. At a dose of 12.5 ug VIP/5 ul Ringer's solution (2.55 ug/ul), 2 rats of 8 treated were discovered dead. At a dose of 25 ug VIP/5 ul (5 ug/ul), there were 4 of 6 documented deaths. At 60 ug VIP/5 ul (12 ug/ul), there were 3 of 5 documented deaths. The progress of illness in these VIP-treated rats was stereotypical to the progress observed following treatment with peptide T. For example, all VIP-treated animals showed diarrhea, weight loss, monoparesis, lower limb deficits and mucous secretions.

The results obtained upon treatment with gp120 may not be as consistent as those obtained upon treatment with peptide T or VIP. Of the seven rats tested with 0.2 ng gp120/ul as discussed above, the monoparesis observed appeared only intermittently during the first two hours, and then persisted for the next 3–4 hours. Of the two rats treated with 0.2 ng/ul gp120, Nos. 6 and 7 in Table IV, only one rat was witnessed to have hemiparesis. Administration of drugs such as VIP or peptide T at doses of 25 ug/5 ul (5 ug/ul) was observed to produce AIDS-like symptoms in addition to neurological deficit including diarrhea, hind limb rigidity and damage to spinal tissue. Deficits such as hindlimb rigidity, arching of the back and difficulty walking were observed following IT administration.

Preliminary data suggest that repeated administration produces further neurological deficits. Moreover, the AIDS virus itself presumably enters the nervous system continuously. The present model accommodates repeated or continuous infusion of peptide T, VIP or gp120 or peptide derivatives or analogs thereof, even while the drug being tested is infused.

The immediate effect produced on the nervous system as a result of intrathecal treatment with gp120, peptide T and VIP indicates that there is a specific receptor to which these compounds are binding. More specifically, the AIDS-like symptoms observed suggest that these molecules are activating the receptor site where HIV binds and produces cellular toxicity. Endogenous VIP may be related to the neurological deficits produced. As such, the present animal model would be highly effective in the screening of a drug for the treatment of AIDS. Research on developing anti-AIDS drugs, moreover, could be directed to this specific receptor. Research on anti-VIP drugs could prove particularly useful. Furthermore, as neurological deficits are shown to be prominent responses, the present animal model may be used for the screening of drugs which may be effective for various neurodegenerative disorders.

The animals treated with peptide T and VIP demonstrated a more dramatic illness one and two days after injection than those receiving 1 ng. gp120. Interestingly, the administration of gp120 did not produce any observed morbidity, whereas morbidity was observed with peptide T and VIP. Generally, rats treated with gp120 exhibited only symptoms of hemiparesis or hind limb rigidity shortly after administration. The resulting symptoms were not as consistently shown as those seen with peptide T or VIP. Additional symptoms, such as hindlimb rigidity, arching of the back and difficulty walking were observed several hours after injection of gp120. In contrast, rats treated with peptide T generally exhibited hemiparesis as the initial response, followed by further problems with the hindlimbs and then mucous and blood secretion, within a time period of about seven hours. Moreover, rats treated with peptide T or VIP were often sacrificed in view of their condition. Given these results, peptide T and VIP may bind more potently to the neurologically active site than does gp120. Other derivatives or analogs of gp120 are also likely to provide a stronger response than that provided by gp120. Moreover, testing with VIP was observed to produce similar results to those obtained with peptide T. Accordingly, intrathecal treatment according to the present invention is preferred with peptide T, VIP or peptide analogs of gp120 rather than with gp120. More pronounced symptoms are shown to be induced upon treatment with peptide T, VIP or derivatives or analogs of gp120, rendering them the preferred animal models over treatment with gp120.

Potential drugs for the treatment of AIDS may be administered after induction of the response. These drugs may be injected through the end of the intrathecal tube exposed through the skin or administered systemically. The animals are then observed for the effect of the drugs in reducing or eliminating the symptoms present in the animal model. In this way drugs are screened in a fast and reliable manner. Once anti-AIDS drugs are identified by using the animal model of the present invention, they may be formulated as treatments for intrathecal injection via hypodermic needle or like means or for systemic injection. Neural effects of HIV infection may be treatable by direct application, i.e., intrathecal administration, of anti-AIDS drugs to the spinal cord. Potential drugs for the treatment of other neurological disorders could be tested in this way also.

Alternatively, a potential drug for the treatment of AIDS may be administered systemically or intrathecally prior to the administration of peptide T, VIP, gp120 or a derivative or peptide analog thereof. In this way, the drug may be tested peptide analog thereof to the active site. In like fashion, once anti-AIDS drugs are identified, they may be administered prophylactically to individuals as a receptor antagonist to the AIDS virus. Moreover, this treatment could prevent or alleviate the undesirable influx of calcium ions into the cell as caused by HIV. Potential drugs for the treatment of other neurological disorders could also be tested by administration of the drug to the animal prior to infusing peptide T, VIP, gp 120 or derivative or peptide analog thereof.

Slow-release administration of anti-AIDS drugs into the spinal cord would be particularly effective in patients in need of treatment. Such drug delivery systems are available commercially.

It will be recognized that the present invention may be practiced with non-human mammals other than rats. It is within the knowledge of those skilled in the art to obtain effective concentrations for other non-human mammals based upon the concentrations set forth herein for rats.

Materials utilized in the present invention are available commercially. Peptide T as well as the complete VIP peptide and fragments thereof may be obtained from Peninsula Laboratories. Gp120 may be obtained from the National Institutes of Health, U.S. Department of Health and Human Services.

The disclosed method permits testing of potential anti-AIDS drugs easily and effectively without handling of the live HIV virus. Moreover, the procedure is relatively simple, requiring knowledge of basic surgical skills and behavioral observation.

What is claimed is:

1. A method of inducing symptoms in a non-human mammal similar to those in AIDS-infected individuals comprising administering to said mammal a material selected from the group consisting of peptide T, VIP, and gp120 intrathecally in an amount effective to induce said symptoms.

2. A method of inducing at least one symptom of neurological deficit in a non-human mammal comprising administering to said mammal a material selected from the group consisting of peptide T, VIP, and gp120 intrathecally in an amount effective to induce said at least one symptom.

3. A method of inducing at least one symptom of neurological deficit in a non-human mammal comprising:
    anaesthetizing said non-human mammal;
    incising the cisterna magna membrane;
    inserting polyethylene tubing into the subarachnoid space of the spinal cord such that one end of said tubing is disposed at the lower spinal cord region and the other end of said tube is exposed through the skin; and
    infusing a material selected from the group consisting of peptide T, VIP, and gp120 through said exposed end of said tubing in an amount effective to induce said at least one symptom.

4. A method as claimed in claim 1 in which said symptoms are induced within about 1 to about 60 minutes of administering a material selected from the group consisting of peptide T, VIP, and gp120.

5. A method as claimed in claim 2 in which at least one symptom of neurological deficit is induced within about 1 to about 60 minutes of administering a material selected from the group consisting of peptide T, VIP and gp 120.

6. A method as claimed in claim 3 in which at least one symptom of neurological deficit is induced within about 1 to about 60 minutes of administering a material selected from the group consisting of peptide T, VIP and gp 120.

7. A method as claimed in claim 1 where gp120 is administered at about 1 ng.

8. A method as claimed in claim 2 where gp120 is administered at about 1 ng.

9. A method as claimed in claim 3 where gp120 is administered at about 1 ng.

10. A method as claimed in claim 1 where peptide T is administered at about 2.55 ug/ul to about 5 ug/ul.

11. A method as claimed in claim 2 where peptide T is administered at about 2.55 ug/ul to about 5 ug/ul.

12. A method as claimed in claim 3 where peptide T is administered at about 2.55 ug/ul to about 5 ug/ul.

13. A method as claimed in claim 1 in which the symptom similar to those in AIDS-infected individuals in selected from the group consisting of hemiparesis, diarrhea, weight loss, hind limb rigidity, arching of the back and difficulty walking.

14. A method of screening drugs for the treatment of AIDS comprising:
    administering to said mammal a material selected from the group consisting of peptide T, VIP, and gp120 intrathecally in an amount effective to induce symptoms similar to those in AIDS-infected individuals;
    administering anti-AIDS drug; and
    determining the effect of said drug on said symptoms.

15. A method as claimed in claim 1 in which a material selected from the group consisting of peptide T, VIP, and gp120 is administered by slow release.

16. A method as claimed in claim 2 in which a material selected from the group consisting of peptide T, VIP, and gp120 is administered by slow release.

17. A method as claimed in claim 3 in which a material selected from the group consisting of peptide T, VIP, and gp120 is administered by slow release.

18. A method as claimed in claim 14 in which a material selected from the group consisting of peptide T, VIP, and gp120 is administered by slow release.

19. A method as claimed of claim 14 in which said drug is administered by slow release.

20. A method as claimed in claim 14 in which said drug is administered to a non-human mammal within about 7 hours of administration of a material selected from the group consisting of peptide T, VIP, and gp120.

21. A method as claimed in claim 14 wherein said drug is administered to said non-human mammal prior to said administration of a material selected from the group consisting of peptide T, VIP, and gp120.

22. A method as claimed in claim 14 in which said symptoms similar to those in AIDS-infected individuals comprise at least one symptom of neurological deficit.

23. A method as claimed in claim 1 where VIP is administered at about 2.55 ug/ul to about 12 ug/ul.

24. A method as claimed in claim 2 where VIP is administered at about 2.55 ug/ul to about 12 ug/ul.

25. A method as claimed in claim 3 where VIP is administered at about 2.55 ug/ul to about 12 ug/ul.

26. A method as claimed in claim 1 where peptide T is administered at about 2.55 ug/ul to about 10 ug/ul.

27. A method as claimed in claim 2 where peptide T is administered at about 2.55 ug/ul to about 10 ug/ul.

28. A method as claimed in claim 3 where peptide T is administered at about 2.55 ug/ul to about 10 ug/ul.

* * * * *

UNITED STATES PATENT AND TRADEMARK OFFICE
CERTIFICATE OF CORRECTION

PATENT NO. : 5,641,746
DATED : June 24, 1997
INVENTOR(S) : Judith L. Steinman

It is certified that error appears in the above-identified patent and that said Letters Patent is hereby corrected as shown below:

On the cover page: Item [19] change to read -- Steinman, et al

Item [75] insert as a joint inventor --Barry Komisaruk, Maplewood, New Jersey--.

Signed and Sealed this

Fifth Day of January, 1999

Attest:

Attesting Officer

*Acting Commissioner of Patents and Trademarks*